United States Patent [19]

Zwemstra

[11] Plant 4,034

[45] Apr. 5, 1977

[54] ROSE PLANT—LIFIRANE VARIETY

[76] Inventor: Jelle J. Zwemstra, Galgeweg 24, Postbus 35, Naaldwijk, Netherlands

[21] Appl. No.: 669,745

[22] Filed: Mar. 24, 1976

[30] Foreign Application Priority Data

Mar. 26, 1975 Netherlands ..... 75S2853
Oct. 30, 1975 Morocco ..... 17282

[51] Int. Cl.[2] ..... A01H 5/00
[52] U.S. Cl. ..... Plt./19
[58] Field of Search ..... Plt./19

*Primary Examiner*—Robert E. Bagwill
*Attorney, Agent, or Firm*—Burns, Doane, Swecker & Mathis

[57] ABSTRACT

A new rose plant of the Grandiflora Class, with double flowers is provided. The rose-plant arose as a bud mutation of the Sweet Promise variety and has flowers which are Rose Neyron in color rather than the usual flowers which are Porcelain pink touched with Begonia pink in depth.

14 Drawing Figures

The object of the present invention is a variety of rose-plant, of the Grandiflora Class, whose vegetative type corresponds to that of the variety Sweet Promise, but whose flowers, although they are of the same form, are distinguishable because of a Rose Neyron color, instead of Porcelain pink touched up with Begonia pink in depth.

The variety of Rose-plant, object of the present invention, is the result of a selective study carried on numerous plants formed by grafting the new matter (new eye) arising from a bud mutation of said variety Sweet Promise.

Indeed, considering the interest that would be created, in the horticultural Industry, by the disclosure of the different technical effect presented by the new variety as compared with the original variety, it was advisable to propagate the said new variety on a large scale, in order to verify its behaviour, from the physical as well as the biological point of view.

The results were conclusive and underlined the importance of disclosing such a variety, with a view to its industrial exploitation by the professional nurserymen and the producers of cut flowers.

The characters and properties of this new variety, obtained as indicated above, are strictly transmissible by agamic means, also called asexual, i.e. by any and all means of vegetative multiplication, in particular by grafting an "eye" which will be called in the trade by the name of eye of Lifirane 0943F.NL, and which will be found on industrial plants as well as on cut stems delivered subsequently in the trade.

DESCRIPTION OF THE DRAWINGS

In order to allow of the identification of this Grandiflora rose-plant, with double Rose Neyron flowers, there is attached to this description, as a sample, a photographic reproduction of the distinctive elements of the plant and of its flower, representing:

FIG. 14 specimens of buds, flowers and leaves.

Figures 1, 2, 3, 4, 5, 6, 7, 8, 9, 10, 11, 12, 13:
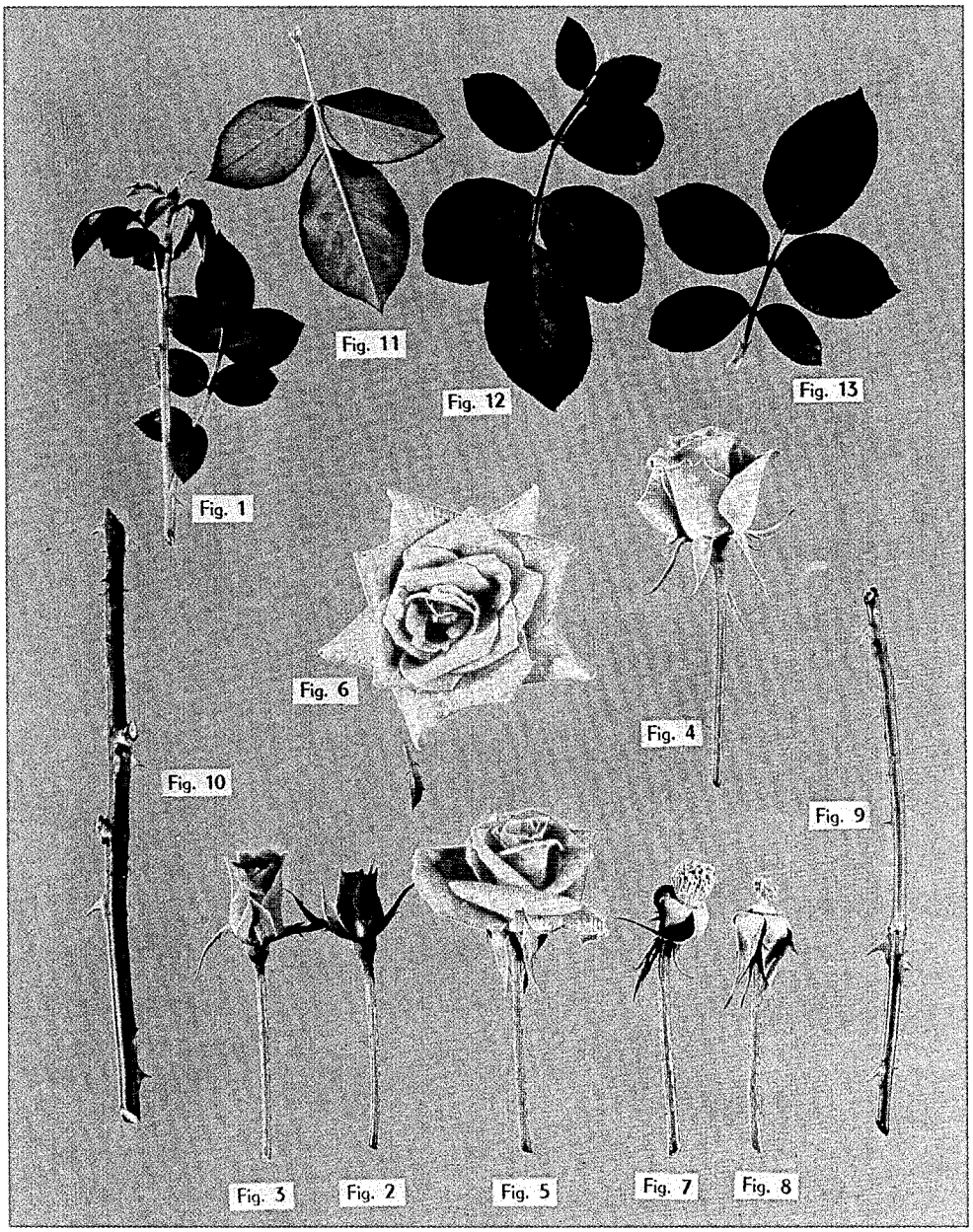
FIG. 1 a specimen of young shoot.
FIG. 2 a specimen of a bud when the sepals burst open.
FIG. 3 a specimen of a bud when the first petal bursts open.
FIG. 4 a specimen of an open bud.
FIG. 5 a specimen of a flower half open.
FIG. 6 a specimen of a flower fully open.
FIG. 7 a specimen of a receptacle at the dehiscence of the anthers, showing the disposition of the stamens.
FIG. 8 a specimen of receptacle showing the disposition of the pistils (stamens removed).
FIG. 9 a portion of a flowering stem.
FIG. 10 a portion of a main branch.
FIG. 11 a specimen of a leaf with 3 folioles, upper surface.
FIG. 12 a specimen of a leaf with 5 folioles, upper surface.
FIG. 13 a specimen of a leaf with 7 folioles, upper surface.

Thus will be obtained once again the rose variety — object of the patent — whose botanical and descriptive characteristics as observed on plants grown under glass, in Holland, are listed below:

DESCRIPTION

The Chart used for the identification of the colors is that of the Royal Horticultural Society (R.H.S. Color Chart). The terminology preceding the numbered references, proper to this Chart, has been added to designate, in common terms, the corresponding colors:

Class: Grandiflora.

Plant:

*Height.*—On the basis of cutting back plants under glass to 0m. 85, the length of the flowering stems to be cut comes to 50/70cms — as with Sweet Promise.

*Habit.*—Erect.

Branches:

*Color.*—Young stems: Lettuce Green 144/B yellow green group. Mature Wood: Spinach Green 146/B yellow green group.

*Prickles.*—Shape: Upper edge: straight, sometimes slightly hooked. lower edge: concave. Size: Medium. Quantity: average, often intermixed with acicules. Color: On young stems: reddish, sometimes very light green; On mature wood: straw, then Havana brown.

Leaves:

*Stipules.*—Adnate, pectinate, long (⅔ of the petiole) sometimes fairly wide.

*Petiole.*—Obverse: young leaf: light green; the edge of the groove is lightly tinted with red. Adult leaf: light green, edges slightly glandular. Reverse: light green, sometimes with tiny hooked prickles.

*Folioles.*—Number: 3, 5 or 7. Shape: Elliptical, with pointed tip. Length of a leaf with 7 folioles: 140mm. Width of a leaf with 7 folioles: 105mm. Teeth: Single and even. Texture: leathery. General effect: Dull foliage, fairly ample and relatively dense.

*Color.*—Young foliage — Upper surface: Light green 137/C green group. The central vein and the teeth of the edges of the petioles and the leaves are tinted with red. Under surface: Green 138/B, green group, more or less stained with reddish on the periphery. Adult foliage — Upper surface: Medium green 137/A green group. Under surface: Greyish green 191/B greyed green group.

Inflorescence:

*Number of flowers.*—Generally one flower per stem.

*Peduncle.*—Light green, fairly rigid. It shows numerous small pediculate glands as well as a few tiny prickles without any consistence. Length: 8, 10 cms. on an average.

*Sepals.*—Normal, very tapered, slightly appendiculate. They are hairy and whitish inside, light green with numerous small pedicellate glands outside. Length: 32 mm. Width: 9 mm.

*Bud.*—Shape: Elongated, slightly cylindrical. Length: When sepals open: 2.8 cm. outside the calyx. Width: 1.7 cm. Size: Medium. Color: When opening—Inside: Carmine Red 52/A (Red group) more or less dark on the edges. Outside: Dark red 51/A Red group.

*Flower.*—Form: First of all elongated, high-centered then, when open, projecting and overlapping petals. Double flower. Diameter: 8 cm. on an average.

*Color.*—When opening—Inside: Carmine Red 52/A (red group). Outside: Pink Red 58/B (Red purple group) more or less shaded with Dark Red 51/A (Red group) on the edges. Greenish unguis. In the course of opening—Inside: Rose Neyron 58/C (red purple group) and Carmine Pink 52/B (Red group) in depth. Yellow unguis. Outside: Rose Neyron 58/C (Red purple group) in depth.

Greenish unguis. When fully blown—Inside: Carmine Pink 58/D (Red Purple Group) in depth—more or less veined with Carmine pink (red group). Yellow unguis. Outside: Carmine Pink 58/D (Red Purple group) in depth. Yellowish unguis.

*Fragrance.*—Very light.

*Lasting quality.*—Long lasting when cut, or on the plant.

*Corolla.*—Petals—Texture: Consistent. Shape: Broadly rounded but somewhat wavy towards the tip. All the petals are more or less folded in a point; The center ones are not always entire and may present some whitish veins. The unguis is yellowish (common term) on both surfaces. Number: from 25 to 30. The petals drop off cleanly.

*Stamens.*—Number: average 110. Anthers: normal, yellow. Filaments: irregular length; they are yellow, sometimes tinted with pink.

*Pistils.*—Number: 70 on an average. Stigmas: Whitish. Styles: Yellowish at base, they become fuchsine at the top. They can be more or less twisted. They are on the same level as the stamens.

*Receptacle.*—Light green, smooth, with a few small pedicellate glands towards the peduncle. It is, in longitudinal section, narrow and in the shape of a pitcher.

Development:

*Vegetation.*—Very vigourous.

*Capacity for reblooming.*—Excellent.

*Resistance to diseases.*—Very great.

I claim:

1. A new and distinct variety of Grandiflora rose-plant of vegetative reproduction characterized by the fact that, from the physical point of view, the plant with Spinach green adult wood, is erect, the flower is double, Rose Neyron in color, the petals are consistent and give the flower a form which initially is high-centered, and when open a form wherein the petals are projecting and overlapping, from the biological point of view, this rose-plant is of vigorous vegetation, its capacity for re-blooming is excellent, and its flowers last a long time whether cut or on the plant, substantially as shown and described.

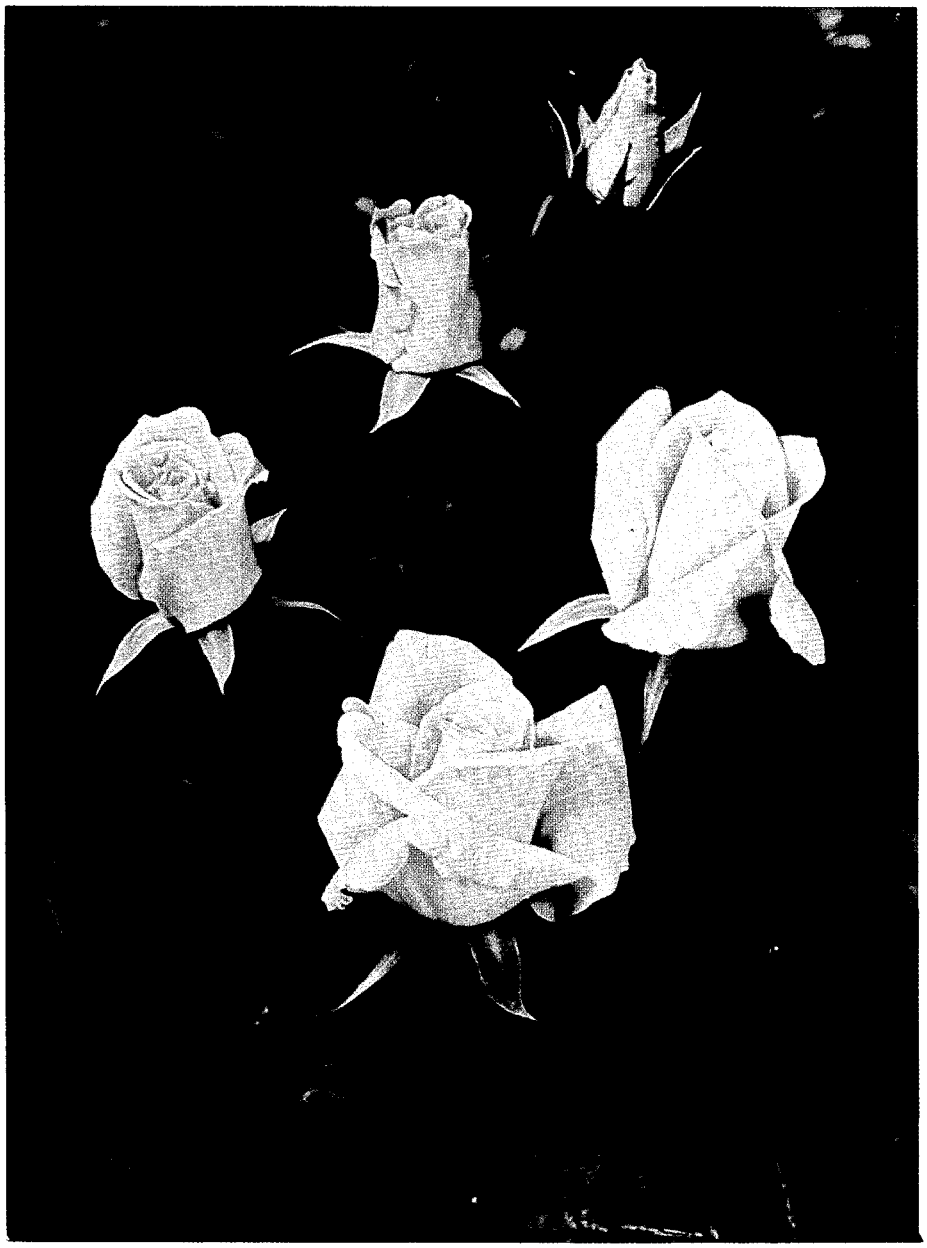

* * * * *